United States Patent
Chee et al.

(10) Patent No.: US 6,641,553 B1
(45) Date of Patent: Nov. 4, 2003

(54) DEVICES AND METHODS FOR DELIVERING A DRUG

(75) Inventors: U. Hiram Chee, Santa Cruz, CA (US); Richard Meuller, Byron, CA (US)

(73) Assignee: Boston Scientific Corporation, Natick, MA (US)

( * ) Notice: Subject to any disclaimer, the term of this patent is extended or adjusted under 35 U.S.C. 154(b) by 200 days.

(21) Appl. No.: 09/585,983

(22) Filed: Jun. 2, 2000

Related U.S. Application Data
(60) Provisional application No. 60/137,265, filed on Jun. 2, 1999.

(51) Int. Cl.[7] .................................................. A61M 5/30
(52) U.S. Cl. .......................................................... 604/68
(58) Field of Search ................................ 604/68, 69, 70, 604/71, 72, 131, 140, 141, 143, 145, 146, 147, 151, 152, 154, 246–249, 256

(56) References Cited

U.S. PATENT DOCUMENTS

| | | | |
|---|---|---|---|
| 2,491,978 A | | 12/1949 | Helfman et al. |
| 2,699,166 A | * | 1/1955 | Dickinson, Jr. et al. ...... 604/70 |
| 3,057,349 A | * | 10/1962 | Ismach ........................ 239/337 |
| 3,424,154 A | * | 1/1969 | Kinsley ....................... 285/298 |
| 3,773,034 A | | 11/1973 | Burns et al. |
| 3,859,996 A | * | 1/1975 | Mizzy et al. ................ 141/352 |
| 3,952,742 A | | 4/1976 | Taylor |
| 4,171,852 A | | 10/1979 | Haentjens |
| 4,243,035 A | | 1/1981 | Barrett |
| 4,266,541 A | | 5/1981 | Landau |
| 4,296,100 A | | 10/1981 | Franco |
| 4,447,225 A | | 5/1984 | Taff et al. |

(List continued on next page.)

FOREIGN PATENT DOCUMENTS

| | | |
|---|---|---|
| EP | 489 496 | 6/1992 |
| WO | WO 92/10142 | 6/1992 |

(List continued on next page.)

OTHER PUBLICATIONS

Boretos, J.W., "Improved intravascular delivery of drug via a polyethylene jet catheter" *13th Annual Meeting of the Society for Biomaterials* Jun. 2–6 pp. 128 (1987).

(List continued on next page.)

*Primary Examiner*—Gene Mancene
*Assistant Examiner*—Huyen Le (57) ABSTRACT

The present invention provides for the needleless delivery of selected agents to target tissues within a subject body by providing the agents in one or more high-energy jets or streams directed against selected wall or surface regions of such tissues. One general embodiment of the apparatus includes (i) an elongate jacket having (a) proximal and distal ends, (b) a lumen extending between such ends, and (c) a blunt, distal-end face defining one or more outlet ports in fluid communication with the lumen; (ii) an introduction port for feeding such agent(s) into the lumen; and (iii) a pump communicating with a proximal end of the jacket. The pump is operable to generate an increased pressure within the lumen such that an agent introduced therein will be propelled out of the distal outlet port(s), thereby forming respective high-energy, narrow, fluid jets or streams capable of penetrating a selected tissue. In an exemplary use, wherein a patient's heart is treated with an agent for transferring genetic information to the heart tissue, the distal end of the jacket is positioned adjacent a selected region of the heart wall, and high-energy fluid jets are directed thereagainst in a manner effective to penetrate the wall, thereby delivering the agent into the myocardium.

31 Claims, 8 Drawing Sheets

U.S. PATENT DOCUMENTS

| | | |
|---|---|---|
| 4,531,936 A | 7/1985 | Gordon |
| 4,576,591 A | 3/1986 | Kaye et al. |
| 4,657,536 A | 4/1987 | Dorman |
| 4,680,027 A | 7/1987 | Parsons et al. |
| 4,767,416 A | 8/1988 | Wolf et al. |
| 4,770,653 A | 9/1988 | Shturman |
| 4,838,850 A | 6/1989 | Rosengart |
| 4,861,339 A | 8/1989 | Jonischkeit |
| 4,911,148 A | 3/1990 | Sosnowski et al. |
| 4,946,442 A | 8/1990 | Sanagi |
| 4,994,033 A | 2/1991 | Shockey et al. |
| 5,034,003 A | 7/1991 | Denance |
| 5,061,273 A | 10/1991 | Yock |
| 5,064,413 A * | 11/1991 | McKinnon et al. .......... 604/143 |
| 5,100,792 A * | 3/1992 | Sanford et al. .......... 435/173.5 |
| 5,106,370 A | 4/1992 | Stewart |
| 5,114,423 A | 5/1992 | Kasprzyk et al. |
| 5,130,141 A | 7/1992 | Law et al. |
| 5,179,022 A | 1/1993 | Sanford et al. |
| 5,185,004 A | 2/1993 | Lashinski |
| 5,197,946 A | 3/1993 | Tachibana |
| 5,203,772 A | 4/1993 | Hammerslag et al. |
| 5,228,883 A | 7/1993 | Blakely et al. |
| 5,244,460 A | 9/1993 | Unger et al. |
| 5,307,803 A | 5/1994 | Matsuura et al. |
| 5,308,324 A | 5/1994 | Hammerslag et al. |
| 5,322,511 A | 6/1994 | Armbruster et al. |
| 5,328,470 A | 7/1994 | Nabel et al. |
| 5,336,178 A | 8/1994 | Kaplan et al. |
| 5,356,388 A | 10/1994 | Sepetka et al. |
| 5,370,685 A | 12/1994 | Stevens |
| 5,372,587 A | 12/1994 | Hammerslag et al. |
| 5,380,279 A | 1/1995 | Schmidt |
| 5,389,096 A | 2/1995 | Aita et al. |
| 5,395,312 A | 3/1995 | Desai |
| 5,429,131 A | 7/1995 | Scheinman et al. |
| 5,431,168 A | 7/1995 | Webster, Jr. |
| 5,476,100 A | 12/1995 | Galel |
| 5,480,381 A | 1/1996 | Weston |
| 5,480,382 A | 1/1996 | Hammerslag et al. |
| 5,492,119 A | 2/1996 | Abrams |
| 5,499,971 A | 3/1996 | Shapland et al. |
| 5,507,724 A | 4/1996 | Hofmann et al. |
| 5,569,160 A | 10/1996 | Sauer et al. |
| 5,569,217 A | 10/1996 | Luther |
| 5,580,859 A | 12/1996 | Felgner et al. |
| 5,591,195 A | 1/1997 | Taheri et al. |
| 5,630,795 A | 5/1997 | Kuramoto et al. |
| 5,642,730 A | 7/1997 | Baran |
| 5,652,225 A | 7/1997 | Isner |
| 5,653,684 A | 8/1997 | Laptewicz et al. |
| 5,661,133 A | 8/1997 | Leiden et al. |
| 5,698,531 A | 12/1997 | Nabel et al. |
| 5,707,969 A | 1/1998 | Nabel et al. |
| 5,725,523 A | 3/1998 | Mueller |
| 5,739,118 A | 4/1998 | Carrano et al. |
| 5,760,081 A | 6/1998 | Leaf et al. |
| 5,772,590 A | 6/1998 | Webster, Jr. |
| 5,782,239 A | 7/1998 | Webster, Jr. |
| 5,782,802 A | 7/1998 | Landau |
| 5,792,453 A | 8/1998 | Hammond et al. |
| 5,797,870 A | 8/1998 | March et al. |
| 5,803,083 A | 9/1998 | Buck et al. |
| 5,807,306 A | 9/1998 | Shapland et al. |
| 5,820,592 A | 10/1998 | Hammerslag |
| 5,827,216 A | 10/1998 | Igo et al. |
| 5,833,658 A | 11/1998 | Levy et al. |
| 5,836,905 A | 11/1998 | Lemelson et al. |
| 5,837,533 A | 11/1998 | Boutin |
| 5,840,031 A | 11/1998 | Crowley |
| 5,840,059 A | 11/1998 | March et al. |
| 5,840,062 A | 11/1998 | Gumaste et al. |
| 5,843,050 A | 12/1998 | Jones et al. |
| 5,846,221 A | 12/1998 | Snoke et al. |
| 5,846,225 A | 12/1998 | Rosengart et al. |
| 5,854,209 A | 12/1998 | Jacobs, Jr. et al. |
| 5,857,464 A | 1/1999 | Desai |
| 5,860,953 A | 1/1999 | Snoke et al. |
| 5,865,811 A | 2/1999 | Doying, Sr. et al. |
| 5,871,462 A | 2/1999 | Yoder et al. |
| 5,871,495 A | 2/1999 | Mueller |
| 5,876,373 A | 3/1999 | Giba et al. |
| 5,882,332 A | 3/1999 | Wijay |
| 5,885,272 A | 3/1999 | Aita et al. |
| 5,891,086 A | 4/1999 | Weston |
| 5,891,136 A | 4/1999 | McGee et al. |
| 5,935,063 A | 8/1999 | Nguyen |
| 5,941,868 A | 8/1999 | Kaplan et al. |
| 5,951,516 A | 9/1999 | Bunyan |
| 5,971,983 A | 10/1999 | Lesh |
| 5,993,443 A | 11/1999 | Murphy-Chutorian et al. |
| 5,997,509 A | 12/1999 | Rosengart et al. |
| 6,004,269 A | 12/1999 | Crowley et al. |
| 6,006,123 A | 12/1999 | Nguyen et al. |
| 6,007,531 A | 12/1999 | Snoke et al. |
| 6,017,322 A | 1/2000 | Snoke et al. |
| 6,024,703 A | 2/2000 | Zanelli et al. |
| 6,036,677 A | 3/2000 | Javier, Jr. et al. |
| 6,056,716 A * | 5/2000 | D'Antonio et al. .......... 604/134 |
| 6,056,742 A | 5/2000 | Murphy-Chutorian et al. |
| 6,102,887 A | 8/2000 | Altman |
| 6,179,809 B1 * | 1/2001 | Khairkhahan et al. ...... 604/528 |
| 6,344,027 B1 * | 2/2002 | Goll ........................... 604/68 |

FOREIGN PATENT DOCUMENTS

| | | |
|---|---|---|
| WO | WO 94/21237 | 9/1994 |
| WO | WO 94/24263 | 10/1994 |
| WO | WO 97/17099 | 5/1997 |
| WO | WO 97/36633 | 10/1997 |
| WO | WO 97/42998 | 11/1997 |
| WO | WO 97/49450 | 12/1997 |
| WO | WO 98/05307 | 2/1998 |
| WO | WO 98/10750 | 3/1998 |
| WO | WO 98/31409 | 7/1998 |
| WO | WO 98/34657 | 8/1998 |
| WO | WO 98/57695 | 12/1998 |
| WO | WO 98/57696 | 12/1998 |
| WO | WO 99/04704 | 4/1999 |
| WO | WO 00/02612 | 1/2000 |

OTHER PUBLICATIONS

Newman, J.H., and Ross, J.C., "Primary Pulmonary Hypertension: A Look at the Future" *JACC* 14(3):551–555 (1989).

Schumacher, B., et al., "Induction of Neoangiogenesis in Ischemic Myocardium by Human Growth Factors" *Circulation* 97:645–650 (1998).

Seldinger, S.I., "Catheter replacement of the needle in percutaneous arteriography" *Acta Radiologica* 38:368–376 (1953).

* cited by examiner

DEVICES AND METHODS FOR DELIVERING A DRUG

This application claims priority to U.S. Provisional Application No. 60/137,265 filed Jun. 2, 1999, which is incorporated herein by reference in its entirety.

FIELD OF THE INVENTION

The present invention is directed to an apparatus and method for delivering selected therapeutic and/or diagnostic agents to target sites in selected body tissues. More particularly, the invention provides for the needleless delivery of such agents by providing each agent in one or more high-energy jets or streams directed against selected wall or surface regions of selected tissues.

BACKGROUND OF THE INVENTION

Needles have long been popular for delivering therapeutic and diagnostic agents into selected tissues. In a typical use, a needle, having an axial lumen extending therethrough, is passed through the wall of a selected tissue to a desired depth, and an agent is then passed from a holding region (e.g., in a bag, or syringe barrel), disposed in fluid communication with a proximal end of the needle, through the axial lumen and out of the distal end, into the tissue. Perhaps best known for their use in the delivery of agents through the skin, needles have also been widely employed in connection with catheters and endoscope-type devices for delivering agents to various organs and tissues within the body. For example, in a typical catheter-type device, an outer jacket is configured for navigation through a patient's vasculature, e.g., using a pull-wire mechanism operable to deflect the distal-end region of the catheter, as desired. A reciprocally movable shaft, disposed within the jacket, defines an agent-delivery passage connected at its distal end to the proximal end of an agent-delivery needle. By advancing the internal shaft, an operator can cause the distal, pointed end of the needle to pierce a selected region of tissue. An agent can then be passed through the shaft's lumen, e.g., under pressure, to flow out of the needle's distal end and into the tissue.

While convenient and effective for certain purposes, the use of needles as injection devices is not without its disadvantages. For example, tissue damage can occur in the region of needle penetration. Also, as most needle-injection devices use only a single needle, the delivery of an agent thereby is often highly localized to one, relatively small region in the tissue (i.e., the site occupied by the needle's distal end), thus limiting the area/volume of tissue that can be treated with each delivery operation. With particular regard to catheter-type needle-injection devices, such as described above, axial reciprocation of the needle-bearing shaft within the steerable jacket can be hampered, if not entirely prohibited, in situations where the distal-end region of the catheter must be deflected to a great degree, e.g., in efforts to reach remote regions via tortuous pathways of a patient's vasculature, rendering such devices unsuitable for certain applications.

SUMMARY OF THE INVENTION

One aspect of the present invention provides an apparatus for delivering a selected diagnostic or therapeutic agent to a target site within a selected body tissue, such as myocardial tissue of the heart.

In one general embodiment, the apparatus includes an elongate jacket having (a) proximal and distal ends, (b) one or more lumens extending between such ends, and (c) a substantially blunt, distal-end face defining one or more outlet ports communicating with one or more of the lumens. Preferably, each outlet port has a diameter of about 0.025", or less (e.g., from about 0.00025" to about 0.020"). The apparatus further includes a pressure-control source (e.g., a pump) adapted for fluid communication with one or more of the lumens. The pressure-control source is operable to establish an elevated pressure (e.g., up to about 300 psi) within such lumen(s) such that an agent placed therein will be propelled toward, and out of, one or more of the outlet port(s), thereby forming one or more respective fluid jets or streams capable of penetrating a selected tissue disposed adjacent thereto.

The apparatus can further include one or more valves, such as spring-loaded needle-type plungers or the like, each being disposed at location along a distal region of a respective one of the lumens for regulating fluid flow therethrough. The valves can be manually operable, or they can respond automatically to one or more selected events (e.g., reaching a threshold pressure at or near a respective outlet port).

In one embodiment, at least one of the outlet ports has a central, longitudinal axis angled no greater than about 35° in respect to a central, longitudinal axis of the jacket at its distal end. In another embodiment, the central, longitudinal axis of at least one of the outlet ports is oriented substantially parallel to the central, longitudinal axis of the jacket at its distal end. In a further embodiment, one or more outlet ports are configured to provide "side firing" fluid jets or streams.

The structure defining each lumen is configured to withstand an elevated pressure generated in the lumen. For example, in one embodiment, where the jacket defines a lumen, the jacket is adapted to withstand an internal pressure of at least about 300 psi along its proximal end, and at least about 100 psi along its distal end.

The pressure-control source can be a pump, such as a power injector or a hand-operable inflation device. Preferably, the pressure-control source is adapted to generate an internal pressure at a distal end of said jacket, proximate said outlet ports, of at least about 20 psi.

One embodiment of the apparatus incorporates the invention in a catheter-type device. For example, the jacket can be a flexible catheter jacket, including a steerable distal-end region that can be deflected in a manner permitting navigation through the vasculature of a subject body so that the outlet port(s) can be positioned adjacent a wall or surface region of a selected tissue or organ. Or, the catheter-type device can include a fixed shape (bend) at along its distal end to facilitate navigation. In yet another embodiment, a first steerable catheter is slidably maintained within an axial lumen of a second steerable catheter. Another embodiment of the apparatus incorporates the invention in an endoscope-type device. Another embodiment of the apparatus incorporates the invention in an open surgical tool having a bent head to access occluded regions of the tissue to be treated.

Any reasonable number of lumens can extend through the jacket of the apparatus. In one exemplary construction, at least two separate lumens extend through the jacket, each distally terminating at a fluid connection with at least one outlet port. For example, two or more separate lumens can be defined by respective elongate tubes extending through the jacket, with each tube having an internal passage with a diameter of from about 0.010" to about 0.020". Advantageously, this configuration reduces the dead volume in the system. Also, the "on/off" response is optimized, and the pressure limit requirement for the conduit can be readily met.

The distal-end face of the jacket is defined, in one embodiment, by a plate-like member mounted substantially transverse to a longitudinal axis of the jacket at its distal-end region. Further in this embodiment, one or more bores extend through the plate-like member—each defining an outlet port. In an exemplary construction, the plate-like member is formed of a suitable, non-reactive metal; and the bores are formed by laser drilling, and/or photo-chemical machining.

In one embodiment of the invention, the apparatus is embodied in a catheter-type assembly. An elongate catheter sleeve is provided, with the catheter sleeve having (i) proximal and distal ends, and (ii) one or more lumens between such ends. For navigation, the catheter sleeve can incorporate a fixed shape at its distal region, and/or it can incorporate a pull-wire steering mechanism. One of the lumens, in this embodiment, is adapted to removably receive the jacket.

According to one embodiment, the jacket-receiving lumen is further adapted to serve as a guidewire channel, when the jacket is removed therefrom.

In another embodiment, one of the lumens, other than the jacket-receiving lumen, defines a guidewire channel. In one exemplary arrangement, the jacket-receiving lumen and the guidewire channel extend side-by-side from the proximal end to the distal end of the catheter sleeve. In another exemplary arrangement, (i) the jacket-receiving lumen extends from the proximal end to the distal end of said sleeve, and (ii) the guidewire channel is provided near a distal end of the catheter sleeve to enable use of the apparatus as a rapid exchange type catheter.

One embodiment of the catheter-type apparatus further includes means for maintaining the distal end of the jacket at the selected target site within a patient's body while one or more high-energy fluid jets or streams are being directed thereagainst.

A further aspect of the present invention provides an apparatus for delivering one or more selected diagnostic or therapeutic agents to a target site within a selected body tissue, including (i) an elongate jacket having (a) proximal and distal ends, (b) a lumen at least along the distal end of said jacket, and (c) a distal-end face defining one or more outlet ports communicating with said lumen; (ii) an agent-holding region (e.g., a chamber) adapted for fluid communication with said lumen; and (iii) means for moving such agent(s) from said holding region and through said outlet port(s) in a fashion effective to cause the agent(s) to penetrate a selected tissue disposed adjacent thereto.

In one embodiment, for use with one or more selected agents (e.g., DNA) coated on a plurality of carrier particles (e.g., gold particles), the moving means includes a biolistic particle-delivery or bombardment assembly disposed within a distal-end region of said jacket.

In another embodiment, the propelling means includes an ultrasonic transducer disposed across the lumen along a distal-end region of the jacket.

In yet another of its aspects, the present invention provides a method for delivering one or more selected diagnostic or therapeutic agents to a target site within a selected body organ or tissue. One general embodiment of the method includes the step of directing one or more fluid jets or streams against a wall or surface of a selected, internal body organ or tissue, with each jet or stream (i) carrying such agent(s), (ii) having a maximum diameter of about 0.025", or less, as it contacts the wall or surface, and (iii) having an energy sufficient to permit the agent(s) to penetrate the organ or tissue to a depth of at least about 2 mm (preferably about 3–10 mm).

According to one embodiment, a gas is utilized as a partial injectate. For example, a gas can be included with one or more of the fluid jets or streams carrying one or more selected agents, or it can be directed therein from a secondary port. In one preferred embodiment, the gas is absorbable by the selected body organ or tissue. The gas, which can include, for example, $CO_2$, can act as a good accelerator.

The method, as just set forth, can be effected using an agent-delivery apparatus comprised of an elongate jacket having (a) proximal and distal ends, (b) one or more lumens extending between such ends, and (c) a substantially blunt, distal-end face defining one or more outlet ports communicating with one or more of the lumens. The agent or agents are directed from the outlet port(s) against such wall or surface. In one embodiment, each jet or stream is formed by propelling the agent(s) through at least a portion of the lumen and out of one of the outlet ports under condition of an increased pressure at the port (e.g., up to about 100 psi; and preferably between about 20–30 psi).

One or more of the jets or streams can be directed substantially perpendicular to a wall or surface of the selected tissue, and/or they can be directed at an angle (e.g., no greater than about 35° in respect to a line normal to a wall or surface of the tissue).

In one embodiment, the selected tissue is myocardial tissue, and the selected agent is directed against an endocardial wall, a septal wall, or an epicardial wall from a distance no greater than about 5 mm from such wall. Any desired agents can be employed (e.g., nucleic acids, proteins, etc.). For example, one or more agents can selected for desirable angiogenic properties. In one particular embodiment, the selected agent includes naked DNA.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which.

DETAILED DESCRIPTION OF THE INVENTION

The following discussion of the preferred embodiments of the present invention is merely exemplary in nature. Accordingly, this discussion is in no way intended to limit the scope of the invention.

Figure 1:
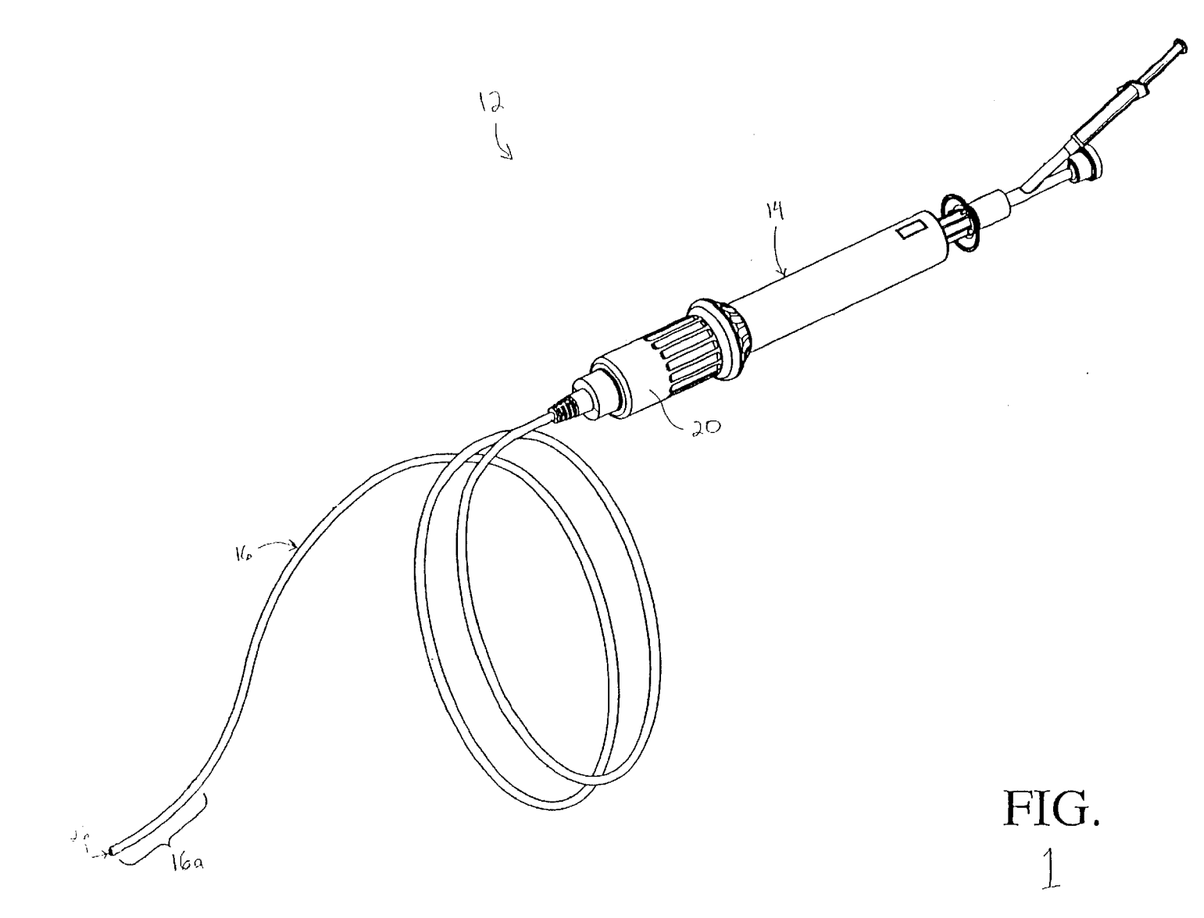
FIG. 1 illustrates a steerable catheter-type device for delivering selected diagnostic and/or therapeutic agents to target sites within a selected body tissue using high-energy jets, in accordance with an embodiment of the present invention.
Figure 11:
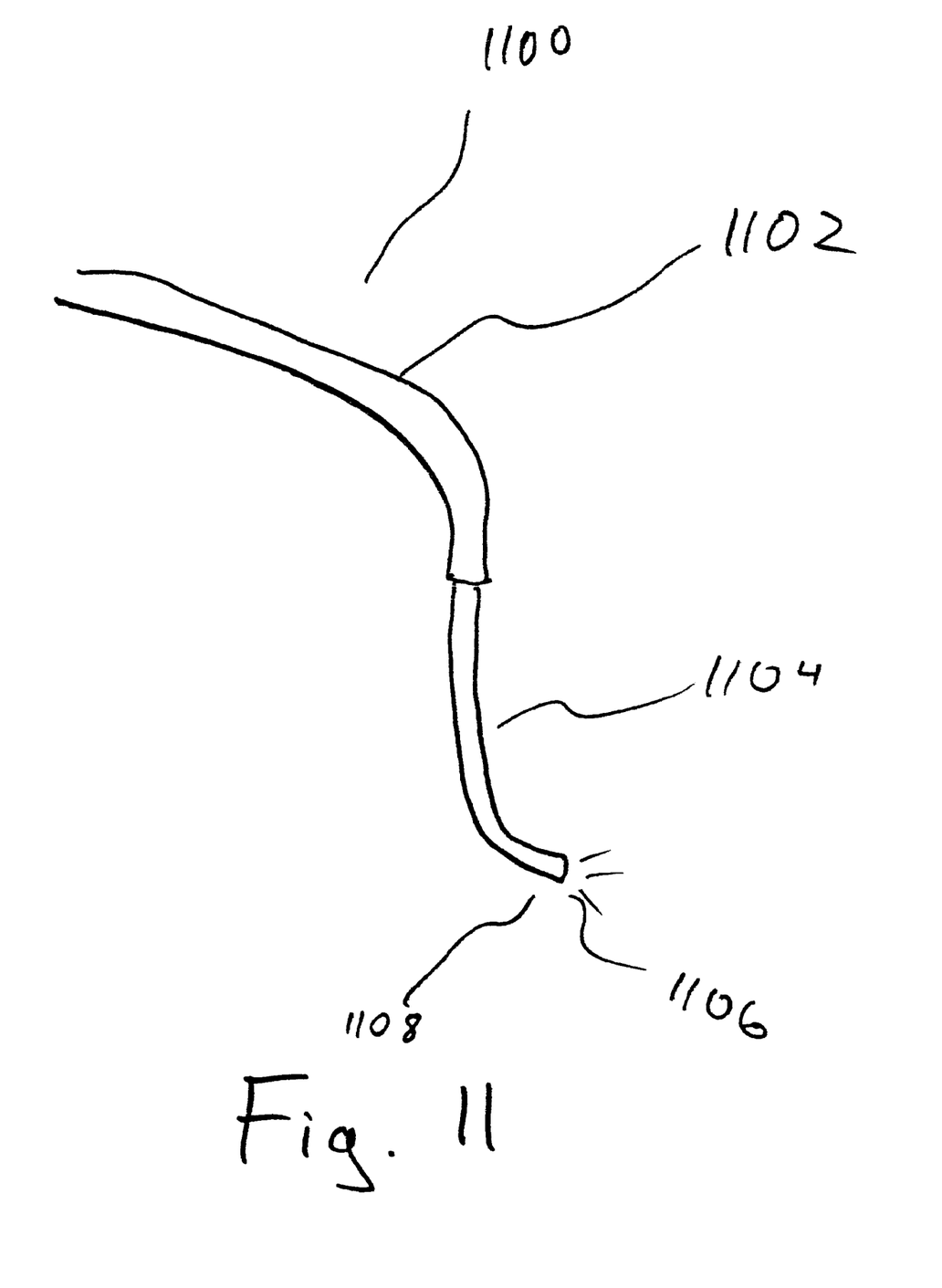
FIG. 11 illustrates an example of the invention where the device is combined with a steerable catheter in one structure.

With initial reference to FIG. 1, a catheter assembly, indicated generally by the reference numeral 12, includes a hand unit 14 attached to a steerable catheter shaft or jacket 16 having a controllably deflectable distal-end portion, as at 16*a*. Steering of the catheter assembly can be accomplished in a variety of ways. For example, the catheter assembly can include steering components like those disclosed in U.S. Pat. No. 5,876,373, entitled "Steerable Catheter," to Giba et al.; and/or in co-pending U.S. patent application Ser. No. 09/080,175, filed May 16, 1998, entitled, "Drug Delivery Module," to Glines et al.; and/or in published European Patent Application No. EP 0 908 194 A2; each of which is incorporated entirely herein by reference. In one exemplary arrangement, a conventional pull wire (not shown) is secured at a distal tip of the jacket and extends through a wire-guide channel, formed longitudinally through a sidewall of the jacket, to the hand unit, whereat the wire's proximal end is coupled to a deflection or steering actuator assembly. Rotation of a deflection knob, such as 20, which is threadedly mounted along a forward end of the hand unit, causes the pull wire to be pulled backward, and/or the jacket to be pushed forward, relative to one another, thereby inducing deflection of the distal end of the jacket. Rather than running the pull wire through a channel extending through a sidewall of the jacket, another embodiment provides the pull wire extending longitudinally along an interior sidewall of the jacket. An advantage of the steerable catheter embodiment of the present invention over Giba's steerable catheter is the ommision of the third inner tool, housed within the second, steerable catheter of Giba. The present invention provides for a unified structure of the tool and steerable catheter making the device simpler, more easily operated, and less costly to manufacture than Giba's triaxial, or coaxial arrangement. Another embodiment of the invention provides for a single catheter unified system where the jet device is integrated into a steerable catheter and omitting the outer, non-steering sheath catheter of Giba, discussed above. Alternatively, the inner tool or fiber optic of Giba may be omitted resulting in a steerable catheter slidably housed within an outer sheath. Other navigation mechanisms and arrangements, suitable for use herein, will be apparent to those skilled in the art. For example, the catheter shaft or jacket can be configured with a fixed shape (e.g., a bend) at its distal end to facilitate navigation as described in application Ser. No. 08/646,856 by Payne filed May 8, 1996, entirely incorporated by reference herein. Another embodiment of the present invention provides for an arrangement that include a dual steering mechanism where both the inner and outer catheter are steerable with either or both catheters steering as a result of either or both having a pull wire or a pre-shaped member. FIG. 11 illustrates a double steerable catheter device 1100, having a first outer steerable catheter 1102 slidably housing a second inner catheter 1104 having a jet discharge tip 1106 located on its distal end 1108.

Jacket 16 is dimensioned to be placed in the vasculature of a subject and navigated therethrough until the distal tip is disposed proximate a surface or wall region of a selected tissue or organ, e.g., within about 5 mm from a surface within a heart chamber (such as the endocardial wall within the heart's left ventricle). The outer diameter of the catheter jacket is not critical, provided only that it can be navigated to a desired site within a subject body. Suitable catheter jackets range in size, for example, from about 3 French to about 9 French. One preferred catheter jacket is 7 French. Suitable catheter jackets are available commercially, for example as guiding catheters and diagnostic catheters from Bard Cardiology; Cordis; and Schneider Worldwide. Certain preferred jackets from such sources include fixed 'shapes at their distal end, instead of pull-wire steering mechanisms.

Visualization enhancement aids, including but not limited to radiopaque markers, tantalum and/or platinum bands, foils, and/or strips may be placed on the various components of the catheter assembly, including on the deflectable end portion 16*a* of catheter jacket 16. Intone embodiment, for example, a radio-opaque marker (not shown) made of platinum or other suitable radio-opaque material is disposed adjacent the distal tip for visualization via fluoroscopy or other methods. In addition, or as an alternative, one or more ultra-sonic transducers can be mounted on the catheter jacket at or near its distal tip to assist in determining its location and/or placement (e.g., degree of perpendicularity) with respect to a selected tissue in a subject, as well as to sense wall contact with, and/or wall thickness of, the tissue. Ultra-sonic transducer assemblies, and methods of using the same, are disclosed, for example, in published Canadian Patent Application No. 2,236,958, entitled, "Ultrasound Device for Axial Ranging," to Zanelli et al., and in co-pending U.S. patent application Ser. No. 08/852,977, filed May 7, 1997, entitled, "Ultrasound Device for Axial Ranging," to Zanelli et al., each of which is incorporated entirely herein by reference. In one embodiment, for example, two transducers are angle mounted at the distal tip of the catheter shaft in the axis or plane of pull-wire deflection. This construction permits an operator to determine, by comparing signal strength, whether the catheter tip region is perpendicular to a selected tissue surface or wall. Additionally, this two-transducer arrangement provides an operator with information useful for determining an appropriate adjustment direction for improving perpendicularity, as compared to single-transducer arrangements that, while capable of indicating perpendicularity by signal strength amplitude, are generally incapable of indicating a suitable direction in which to move the tip to improve perpendicularity. In a related embodiment, third and fourth transducers (not shown) are added, off of the deflection axis, to aid an operator with rotational movement and rotational perpendicularity in the non-deflecting plane of the subject tissue, surface. Additional details of the just-described embodiment are provided in co-pending U.S. patent application Ser. No. 09/566,196 [Attorney Docket No. 5756-0005.30], filed May 5, 2000, entitled, "Apparatus and Method for Delivering Therapeutic and Diagnostic Agents," to R. Mueller; incorporated entirely herein by reference. Ultrasonic transducers may, preferably, be substituted with one or more force contact transducers as described in co-pending U.S. Provisional patent application No. 60/191,610 [Attorney Docket No. 5756-0011], filed Mar. 23, 2000 by Tom, entirely incorporated by reference herein.

Figure 12:
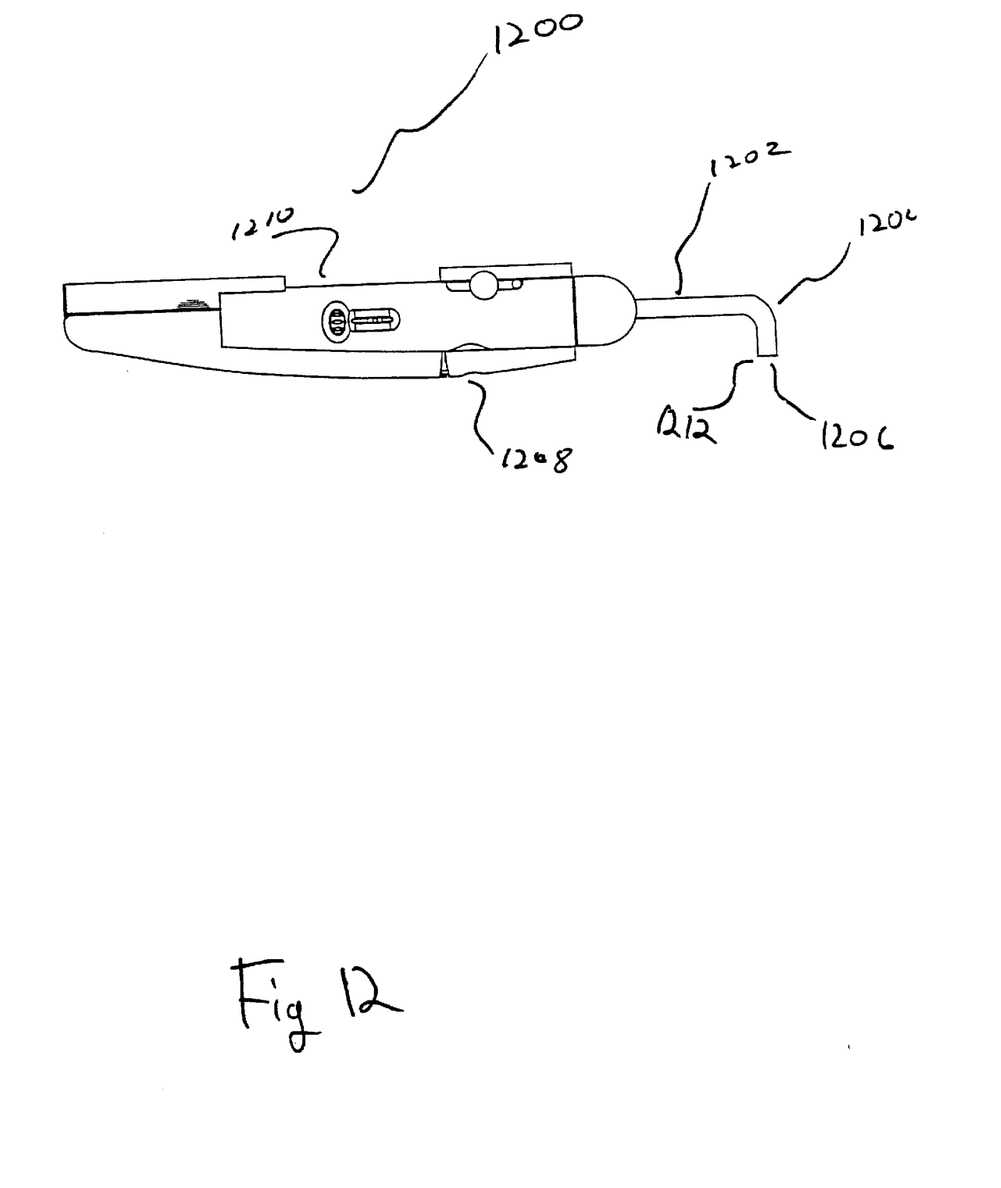
FIG. 12 illustrates an example of the invention where the device is combined with a a first steerable catheter in one structure which resides in a second steerable catheter having an axial lumen where the first steerable catheter is slidably maintained.

With respect to hand held, open surgery devices, it is often important to insure that proper contact force is created between the device and a target tissue before discharging the device. Otherwise, the device may inadvertently discharge as it is manipulated towards a target tissue, or it may, in the case where too much force is applied, cause perforation of a tissue that is thinned out as a result of distention caused by excessive force. A force sensing interlock may be incorporated into the invention thus only permitting discharge when such force is within a certain range, both minimally and maximally. For example, ultrasound transducers, force contact transducers, and mechanical interlocks having a minimal and maximal limit. Consequently, hand held needleless hypodermic injector devices, such as those described in U.S. Pat. Nos. 3,057,349, 3,859,996, 4,266,541, 4,680,027, 5,782,802, each entirely incorporated by reference herein, lacking interlocks altogether, or only providing interlocks that activate at a minimum threshold force, without regard to a maximum force limit, are often inadequate. These hand-held needleless injectors are further limited in that their structure is not amenable for use inside of a patient cavity created by open surgery, thoroscopic or other "portal" procedures. For example, in each of those disclosures provided for a snub nosed hand-held gun for use against a patients skin, typically a shoulder region of a human. The present invention provides for an elongated jacket portion of the tool to facilitate reaching inside a remote region of the patient. The tool distal end may further be angled or bent, either fixedly, or by bending on demand, or by remote steering of the distal region of the tool. FIG. 12 illustrates an open surgical tool where device 1200 has an elongated jacket portion 1202 having a bend portion 1204, ending in jet tip 1206 located at distal end 1212 which is where liquid is ejected when actuator 1208 is compressed thereby causing a liquid reservoir located around 1210 to deliver fluid to tip 1206 through a fluid conduit not shown.

Figure 2A:
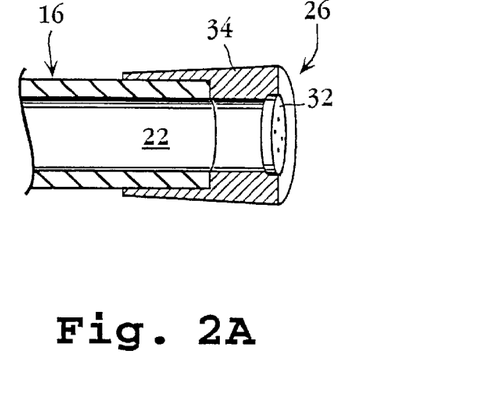
FIG. 2A is an enlarged, side-sectional view of a distal-end region of the device shown in FIG. 1.
Figure 2B:
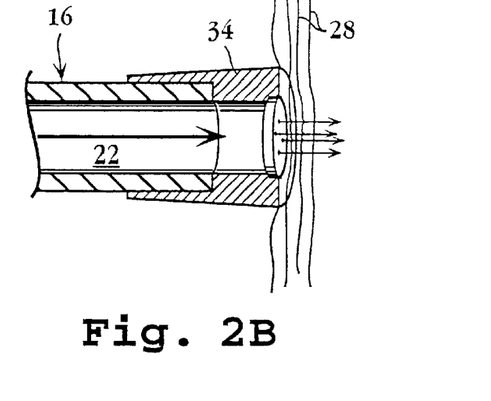
FIG. 2B shows the device of FIGS. 1 and 2A being used to direct four high-energy jets carrying one or more selected therapeutic and/or diagnostic agents through a wall of a selected body organ and into the tissue.
Figure 3:
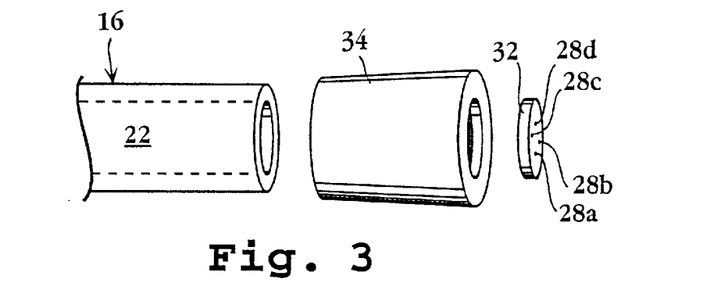
FIG. 3 is an exploded view of the apparatus of FIGS. 2A–2B.
Figure 4:
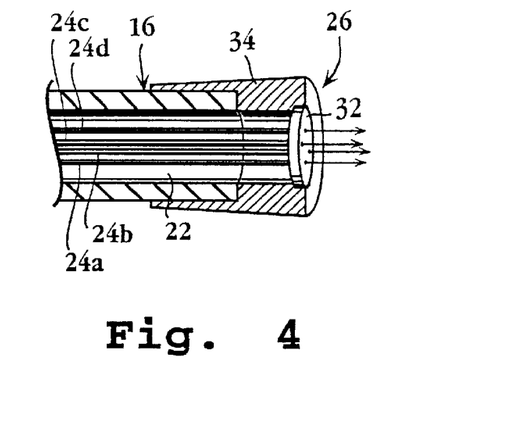
FIG. 4 is a partial, side-sectional view of a further embodiment of an agent-delivery apparatus for delivering selected diagnostic and/or therapeutic agents to target sites within a selected body tissue using high-energy jets, according to the teachings of the present invention.

Internal to the jacket is one or more lumens, extending between the jacket's distal and proximal ends. The lumens serve as passages through which one or more selected agents can pass en route to a selected tissue or organ. In the arrangement of FIGS. 2A, 2B and 3, for example, a single lumen, denoted as 22, extends longitudinally through jacket 16. In another embodiment, shown in FIG. 4, a plurality of elongate tubes, such as 24a–24d, extend through a primary lumen 22 defined by the jacket 16. In this latter embodiment, each of the tubes includes an internal longitudinal conduit or channel, defining a respective sub-lumen or delivery lumen through which one or more agents can pass. Advantageously, this configuration reduces the dead volume in the system. Also, the "on/off" response is optimized, and the pressure limit requirement for the conduit can be readily met.

Catheter jacket 16 terminates at a distal-end face, indicated generally at 26, defining one or more narrow outlet ports or orifices, such as 28a–28d (FIG. 3). Face 26 is configured with a relatively broad distal surface region of sufficient area to accommodate a desired number of outlet ports such that each port can be placed against, or very close to (e.g., within about 5 mm, and preferably within about 2 mm), a selected wall or surface region of a target body organ or tissue. Accordingly, one embodiment provides the distal-end face as a generally blunt structure with a broad distal surface. For example, in FIGS. 2–4, a cylindrical plate 32 defines the distal-end face, with the plate having a distal surface that is substantially planar. Alternatively, the distal surface can be somewhat curved (e.g., convex). One or more bores extend through the plate, between its proximal and distal broad surfaces, defining outlet ports for the passage of selected agents.

The plate can be secured along the distal-end region of the jacket in any suitable manner. In one embodiment, for example, the plate is attached directly to the distal tip of the jacket, or in a counterbore formed from the distal tip. Another embodiment, shown in FIGS. 2–4, contemplates the use of an intermediate adapter plug or cap, denoted as 34, having a proximal end configured to fit snugly over the outer circumference of a distal-end region of jacket 16. The distal portion of the adapter cap includes an annular counterbore, or stepped region, configured to receive a peripheral region of the plate. Adapter cap 34 can be formed of a suitable plastic material, such as polyethylene or nylon, or of a metallic material such as stainless steel, and bonded to the jacket by heat sealing and/or a conventional adhesive, or other bonding means. The outlet port(s) can be formed, for example, by laser boring, photo-chemical machining, or other suitable technique; or the plate and bores can be formed together as a molded component.

With further regard to the outlet ports, each is adapted for communication with one or more of the agent-delivery lumens extending through the jacket. In a preferred embodiment, there from about 1–12 outlet ports (e.g., four, in the illustrated arrangement), each having a diameter of no greater than about 0.025"; and preferably within a range of from about 0.00025" to about 0.020" (e.g., 0.006"). The size and orientation of each outlet port serves to direct agents passed through the catheter lumen(s) in an axial direction, or at an angle no greater than about 35 degrees off axis (i.e., relative to the catheter's longitudinal axis at its distal-end region), in the form of a narrow jet or stream. Axially directed jets or streams can help to maximize penetration depth, while angled jets or streams can help to increase the treated area/volume of tissue. Axially directed jets are illustrated in FIG. 2B, wherein four outlet ports are configured to direct an agent passed through lumen 22 (indicated by the large, darkened arrow) axially into a selected tissue 28 as four separate jets or streams (indicated by the four smaller, substantially parallel arrows).

Figure 6:
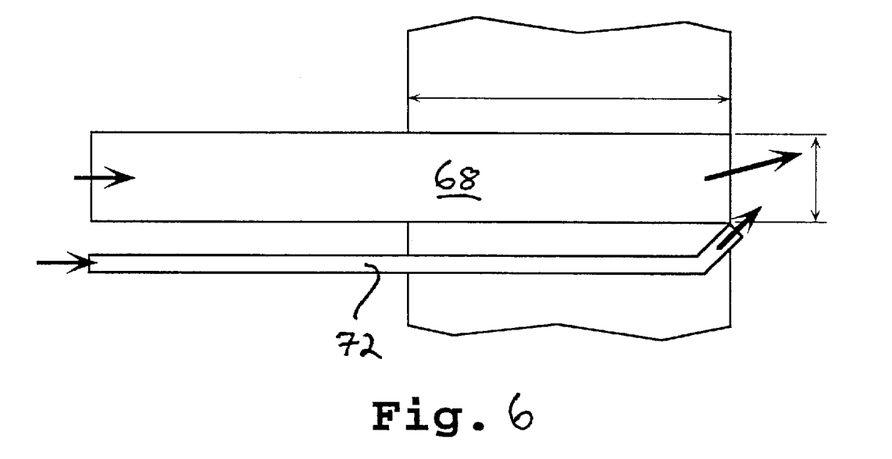
FIG. 6 shows, in partial side-sectional view, an exemplary agent-delivery port and a secondary drug or gas-port that meets the delivery port at an angle, as well as several exemplary jet or spray patterns.
Figure 6A:
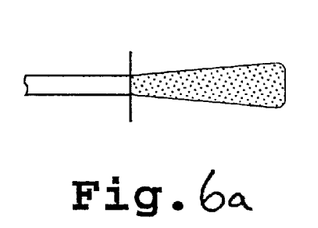
Figure 6B:
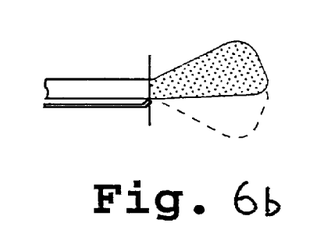
Figure 6C:
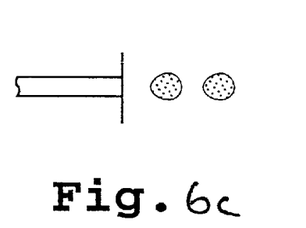

The outlet ports can be configured to achieve desired jet or spray patterns by modifying, for example, the port diameter, length and/or internal shape. The pressure at the port can also be adjusted to influence the patterns. Injection streams can be further modified with secondary injection of additional drug, or a compatible gas, such as $CO_2$ and/or other absorbable gas. Such a gas can be a good accelerator. In addition, a pulsed injection pattern can be employed to capitalize on tissue recoil effects. In these regards, attention is directed to FIG. 6 which shows an exemplary agent-delivery port 68 and a secondary drug or gas port 72 that meets the delivery port 68 at an angle. Also depicted are several exemplary jet or spray patterns, denoted as "A," "B" and "C." Pattern "A" can be achieved by passing an agent through port 68 under pressure, without the use of a secondary port. Pattern "A" is modified to that of pattern "B" by additionally passing an agent or gas through secondary port 72. Pattern "C" is a pulsed spray pattern that can be used to take advantage of tissue recoil effects. This pattern can be achieved by passing an agent through port 68 as rapid, controlled bursts, without the use of a secondary port. FIG. 9 is a partial side view of an example of the invention as it is placed near a tissue (9*a*), urged against the tissue (9*b*) thus creating a contact force between the device and the tissue, the application of hydraulic force causing ejection of a fluid stream from each outlet port thus propelling the fluid into the tissue (9*c*), and the removal of hydraulic force and the retention of fluid by the tissue within pockets created by hydraulic erosion (9*d*).

Figure 7:
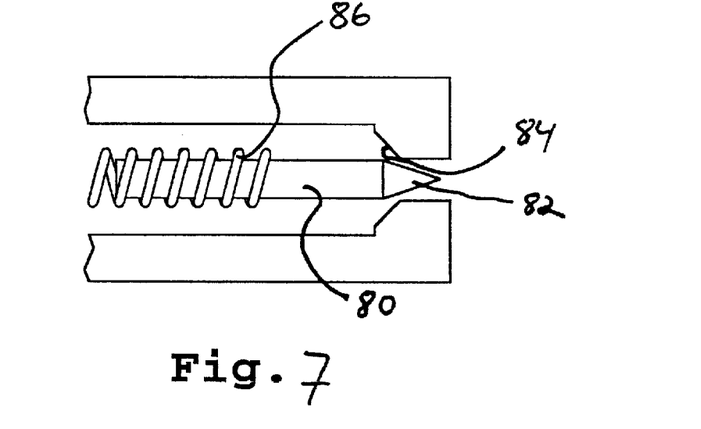
FIG. 7 is a partial side view, with portions shown in section, of an exemplary valving mechanism operable to regulate fluid flow through an agent-delivery lumen and/or outlet port.

In one embodiment, one or more of the agent-delivery lumens and/or outlet ports includes a valving mechanism operable to regulate fluid flow therethrough. Such an arrangement can be useful, for example, for controlling the timing and/or energy of each jet. For example, a quick-action valve can permit controlled, rapid-fire bursts from an outlet port. In one embodiment, a first burst causes a target tissue to recoil and expand, and a subsequent burst then penetrates the tissue while in an expanded state. An exemplary valving mechanism is shown in FIG. 7. Here, an elongate needle plunger 80 has a distal, pointed end 82 that is normally urged against a seat seal 84 by a coil spring 86, thereby closing a respective outlet port. Needle 80 can be withdrawn from seat 84, against the normal bias of spring 86, by pulling on an actuation line (not shown), manually or otherwise, that connects to a proximal end of the needle, thereby opening the port. In another embodiment, a pressure-actuated valving mechanism is employed. Here, the valve is adapted to open automatically upon reaching a certain, predetermined threshold pressure at the port.

As previously indicated, one advantage provided by the present invention is the avoidance of tissue damage often associated with the use of needles. Nevertheless, it should be noted that in certain circumstances a limited amount of tissue damage at or about the injection site may be desirable. For example, where angiogenic agents are being delivered, tissue injury can be beneficial in creating an environment where the action of such agents is enhanced. Thus, it will sometimes be desired to configure the outlet ports to produce jet or spray patterns appropriate for effecting a desired amount of tissue damage over a selected area.

In addition to the lumen arrangements described above with respect to FIGS. 2–4, the present invention further contemplates an assembly including one or more elongate tubular elements that can be removably received within a primary lumen defined by an outer elongate sleeve. Each removable tubular element, in this embodiment, defines a sub-lumen or delivery lumen through which one or more selected agents can pass, and includes a distal-end face defining one or more respective outlet ports. Preferably, each tubular element is adapted to slide longitudinally through the primary lumen of the elongate sleeve for placement therein and removal therefrom, as desired. One embodiment, for example, provides such a tubular element coaxially within an elongate sleeve. The sleeve or the tubular element can incorporate pull-wire steering and/or fixed shapes at their distal end to facilitate navigation. Another embodiment provides such a tubular element extending side-by-side with a guidewire lumen from a proximal to a distal end of an elongate sleeve. In still a further embodiment, such a tubular element is incorporated in a rapid-exchange external-guidewire apparatus. In an exemplary construction of the latter, the tubular element extends longitudinally from a proximal to a distal end of the elongate sleeve, and runs side-by-side with a guidewire lumen along a distal region (e.g., about 3–5 mm) of the sleeve. For example, the present invention can be incorporated in a rapid-exchange apparatus substantially as taught in U.S. Pat. No. 5,061,273; which is incorporated entirely herein by reference. In yet a further embodiment, such a tubular element is adapted to be removed from a lumen extending longitudinally through the sleeve and replaced with a guidewire for facilitating catheter advancement across an anatomical structure such as a heart valve.

In a further exemplary arrangement, a guidewire lumen is coaxial with one or more delivery lumens, with the guidewire lumen at the center and the delivery lumens surrounding the guidewire lumen. It is contemplated that the guidewire lumen can be used to place other elongated devices, if desired, such as ultrasound sensors to measure wall thickness or pressure sensors to infer contact against a wall.

An agent reservoir can be utilized for holding a selected therapeutic and/or diagnostic agent until delivery. The reservoir can be of any suitable type. In one exemplary construction, the reservoir is configured to hold a fluidic agent (e.g., in liquid form) for introduction, using a substantially closed system, into an agent-delivery lumen of the jacket. For example, the agent can be held within a chamber provided inside the catheter jacket, or it can be introduced from an external reservoir, such as a syringe or bag, via a conventional introduction port located along the hand unit or along a proximal region of the jacket. In one embodiment, the hand unit is provided with a fixed internal reservoir for holding a supply of a selected agent to be dispensed. In this embodiment, a supply reservoir, such as a syringe, can communicate with the internal reservoir via a connector provided in the hand unit's outer housing. The connector is preferably a substantially sterile connector, such as a standard Luer-type fitting or other known standard or proprietary connector. In another embodiment, the supply reservoir comprises a syringe, pre-loaded with a selected agent, that can be removably fit into a holding area inside the housing of the hand unit, as taught, for example, in co-pending U.S. patent application Ser. No. 09/080,175, filed May 16, 1998, entitled, "Drug Delivery Module," to Glines et al; incorporated entirely herein by reference.

A pressure-control source is provided in fluid communication with one or more of the agent-delivery lumens. The pressure-control source, e.g., a manual or automatic pump, is operable to establish; an elevated pressure within such lumen(s) such that an agent placed therein will be propelled toward, and out of, one or more of the outlet ports, thereby forming one or more respective fluid jets or streams capable of penetrating a selected tissue disposed adjacent thereto. In one embodiment, the pressure-control source is a hand-operable syringe-type pump, connected to one or more lumens along a proximal end of the jacket. Commercially available pressure-control sources that can be readily adapted for use herein include, for example, power injectors, such as the ACIST Injection System Model CL 100 (ACIST Medical Systems), and inflation devices, such as the ARIA or BREEZE inflation devices from Schneider/Namic (Glen Falls, N.Y.).

An exemplary method of using the above catheter assembly will now be described, wherein the catheter assembly is used for intra-myocardial delivery of a selected therapeutic and/or diagnostic agent. Initially, catheter shaft 16 is percutaneously introduced via femoral or radial artery access. Once arterial access is established, the catheter shaft is slid across the aortic valve and into the left ventricle chamber. The distal end of the catheter shaft is maneuvered so as to be substantially perpendicular to the endocardial wall 28 (FIG. 2B), using fluoroscopic visualization and/or ultrasound guidance, and pressed into contact therewith. A selected agent, in fluidic form, is then introduced into a proximal-end region of lumen 22, and the lumen is pressurized so as to achieve about 200–300 psi along the proximal end with a drop to about 20–100 psi (preferably about 20–30 psi) along the distal end. Under the influence of such pressure, the agent is propelled through the lumen, to and out of one or more outlet ports. In this way, one or more narrow jets or streams are directed at the endocardial wall. Each jet penetrates the tissue to a depth of between about 2–10 mm, and preferably about 5 mm. The injection is carried out over a time period of about 1–15 seconds.

Instead of a catheter-type device, the invention can be incorporated in other percutaneous and/or surgical devices. For example, one embodiment contemplates an endoscope-type device having an elongate shaft with one or more longitudinally extending lumens extending therethrough. As with the catheter-type device, the structure defining each lumen (e.g., the endoscope shaft, or one or more tubes extending through the shaft) is configured to withstand an elevated pressure (e.g., up to 300 psi) in the lumen. Also, like the catheter-type device, a substantially blunt, distal-end face defines one or more outlet ports communicating with one or more of the lumens; with each of the outlet ports having a diameter of about 0.025", or less (e.g., 0.006"). A pressure-control source, such as a pump, is provided in fluid communication with one or more of the lumens, operable to establish an elevated pressure within such lumen(s) such that an agent placed therein will be propelled toward, and out of, one or more of the outlet ports, thereby forming one or more respective fluid jets or streams capable of penetrating a selected tissue disposed adjacent thereto. Various other details pertaining to agent delivery are substantially like those set forth herein with regard to the catheter-type device.

In an exemplary use, the endoscope-type device of the invention is introduced thoracoscopically or through a thoracotomy, to direct high-energy jets at the wall or surface of a selected tissue or organ. For example, one or more high-energy jets can be directed at the epicardial surface of the heart, permitting one or more selected agents to penetrate the myocardial tissue. The surgical device can incorporate a thoracoscopic camera (e.g. a reusable 5 mm camera) axially mounted to provide an operator with a suitable field of view through a lens. This allows the operator to work through a common Trocar access port placed, for example, through a patient's chest wall.

It is noted that the above-described methods are merely exemplary in nature. Those skilled in the art will appreciate that the present invention provides for the delivery of selected agents to a wide variety of body organs and regions.

Figure 5:
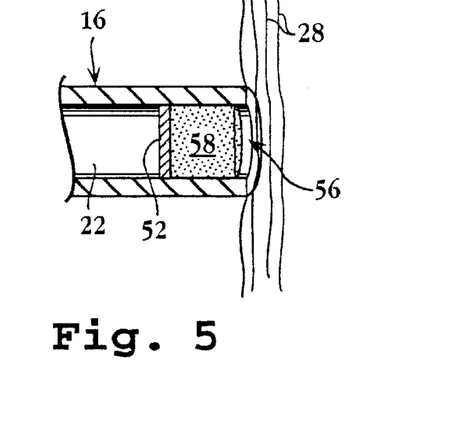
FIG. 5 shows the distal-end region of a steerable catheter-type device for delivering selected diagnostic and/or therapeutic agents to target sites within a selected body tissue using ultrasonic energy, according to one embodiment of the present invention.

In another embodiment of the present invention, a selected therapeutic and/or diagnostic agent is held within a reservoir at the distal-end region of an elongate shaft and delivered into a tissue by means of ultrasonic energy. Pertinent portions of an exemplary agent-delivery apparatus, which can be incorporated in a catheter-type device or an endoscope-type, such as previously described, are shown in FIG. 5. Here, the distal-end region of a catheter-type device is shown, having an ultrasonic transducer 52 (e.g., a piezoelectric transducer, such as barium titanate, lead zirconate titanate, or the like) disposed across lumen 22. The distal end of the catheter jacket defines a single, relatively large opening, denoted as 56; however, a cap or plug with one or more smaller openings (similar to that as described above) can be used instead. The transducer is operable to emit ultrasonic energy, of appropriate intensity (e.g., up to about 6 watts/cm$^2$) and frequency (e.g., up to about 20 MHz), along a generally axial direction toward a wall or surface region of a selected organ or tissue 28 within a subject body. The energy, so applied, is effective to cause an agent 58, held within a holding region near the distal end of the catheter jacket, to move toward and penetrate the tissue wall. In one embodiment, the agent is distributed in a polymer matrix, or other solid or semi-solid form, within the holding region. The agent is maintained in the matrix within the holding region until the time of delivery. Alternatively, the agent (e.g., in liquid or semi-solid form) can be maintained within the holding region until delivery by providing a semi-permeable membrane between the agent and the opening at the distal end of the catheter jacket. Other means for maintaining the agent in the holding region until delivery will be apparent to those skilled in the art.

In another embodiment, a selected therapeutic and/or diagnostic agent is held within a distal-end region of a catheter or endoscope-type device and propelled into a target tissue or organ using a biolistic particle-delivery or bombardment assembly. In one embodiment, the biolistic assembly (e.g., a so-called "gene gun" incorporated along a distal-end region of the agent-delivery device) introduces nucleic acid-coated microparticles, such as DNA-coated metals, into a tissue at high energies. The coated particles can be propelled into the tissue using any suitable means, e.g., an explosive burst of an inert gas e.g., (helium), a mechanical impulse, a centripetal force, and/or an electrostatic force (See, e.g., U.S. Pat. No. 5,100,792 to Sanford et al.; incorporated entirely herein by reference). In an exemplary embodiment, a spark discharge between electrodes placed near, the distal-end region of the catheter, proximal of a distal-end agent-holding region, is employed to vaporize a water droplet deposited therebetween, which then creates a shock wave capable of propelling the DNA-coated particles. The technique allows for the direct, intracellular delivery of DNA. The carrier particles are selected based on their availability in defined particle sizes (e.g., between about 10 and a few micrometers), as well as having a sufficiently high density to achieve the momentum required for cellular penetration. Additionally, the particles used are preferably chemically inert to reduce the likelihood of explosive oxidation of fine microprojectile powders, as well as non-reactive with DNA and other components of the precipitating mixes, and display low toxicity to target cells (See e.g., Particle Bombardment Technology for Gene Transfer, (1994) Yang, N. ed., Oxford University Press, New York, N.Y. pages 10–11; incorporated entirely herein by reference). For example, tungsten and/or gold particle microprojectiles can be employed to achieve adequate gene transfer frequency by such direct injection techniques. Alternatively, or in addition, diamond particles, as well as glass, polystyrene and/or latex beads can be used to carry the DNA. The DNA-coated particles can be maintained in the agent-holding region by any suitable means, e.g., precipitated on the distal face of a carrier sheet suspended across a lumen at or near the distal end of the jacket. In this latter embodiment, the propulsion means propels the DNA-coated particles from a distal face of the carrier sheet into a selected target tissue or organ adjacent thereto.

Figure 8:
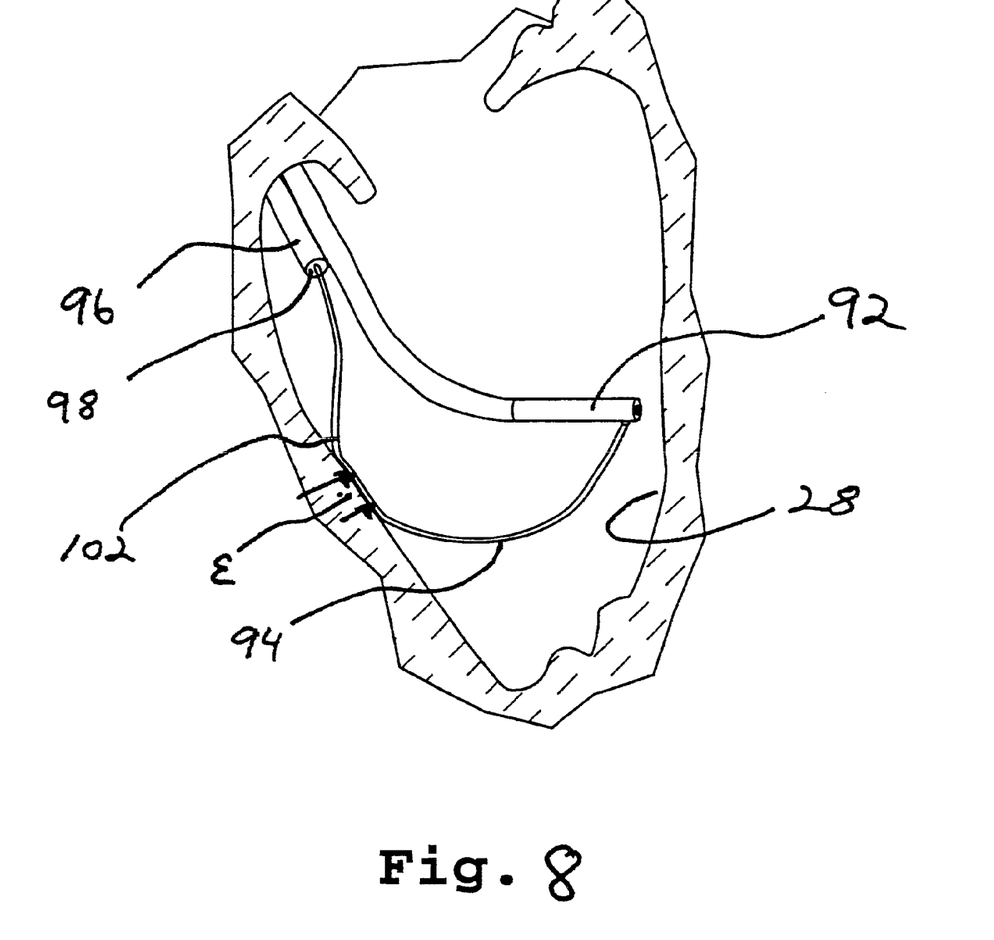
FIG. 8 shows a portion of a steerable catheter positioned with its distal end adjacent a target region of an endocardial wall of a patient's left ventricle, with the catheter being adapted to maintain its distal end at such position notwithstanding "action-reaction" forces due to high-energy jets emanating therefrom that would tend to push it away from the wall.
Figure 9A:
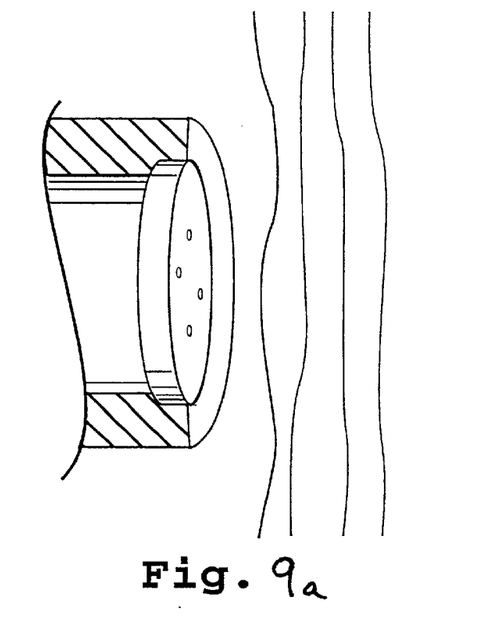
FIG. 9 is a partial side view of an example of the invention as it is placed near a tissue (9*a*), urged against the tissue (9*b*) thus creating a contact force between the device and the tissue, the application of hydraulic force causing ejection of a fluid stream from each outlet port thus propelling the fluid into the tissue (9*c*), and the removal of hydraulic force and the retention of fluid by the tissue within pockets created by hydraulic erosion (9*d*).
Figure 9B:
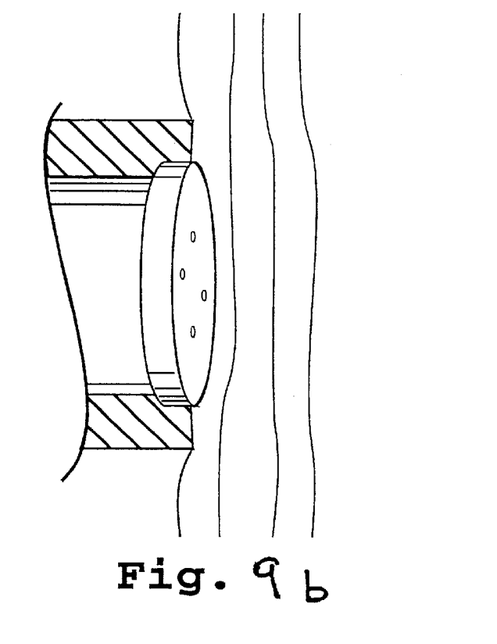
Figure 9C:
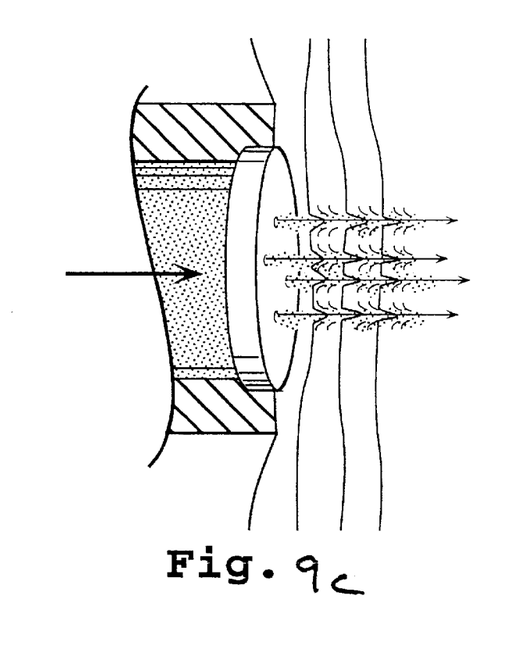
Figure 9D:
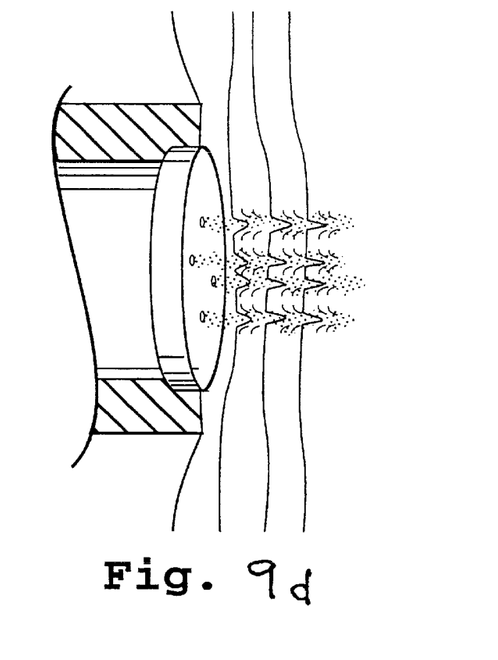
Figure 10A:
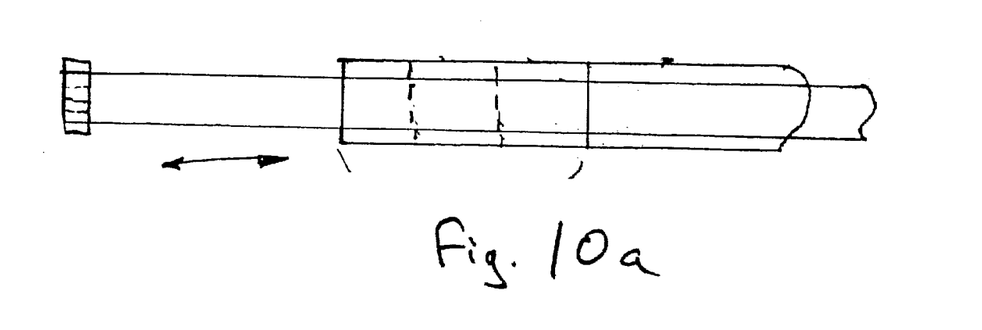
FIG. 10*a* illustrates an example of the invention where a the device is conveyed to the target tissue via a steerable catheter with having an axial lumen where the device is slidably directed towards the target tissue.
Figure 10B:
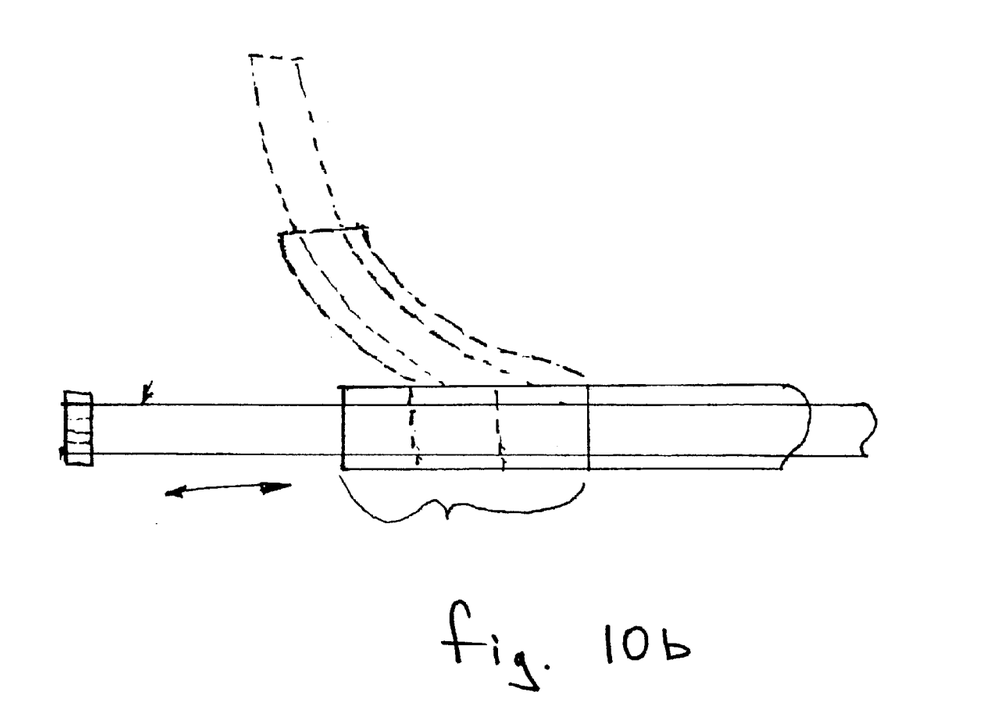
FIG. 10*b* illustrates how the device is "steered" towards a target.

It will be appreciated that, especially with regard to catheter-type delivery apparatuses, an agent directed from a distal end of the apparatus with sufficiently high energy may cause such end to move away from a target tissue wall or surface. FIG. 8, for example, shows a portion of a steerable catheter 92 having a distal end positioned adjacent a target region of an endocardial wall 28 of a patient's left ventricle 94. Arrows "A" and "B" depict an "action-reaction" phenomenon, with (i) arrow "A" representing an injection force provided by one or more high-energy fluid jets or streams directed against the wall 28, with the jet(s) carrying, for example, an angiogenic agent (e.g., "naked" DNA), and (ii) arrow "B" representing a resultant, oppositely-directed force tending to push the distal tip of the catheter away from the endocardial wall. To counter the latter, means are provided for maintaining the distal end of the catheter proximate the endocardial wall. In the illustrated embodiment, a secondary lumen 96 extends longitudinally along the catheter and terminates at a distal orifice 98, short of the catheter's distal end (e.g., by between about 1–4 cm). An elongate wire 102 is slidably received within the secondary lumen 96 and has its distal end attached to the catheter at, or near, the catheter's distal end. From a remote (proximal) location, wire 102 can be moved between a retracted position, with the distal region of the wire positioned closely adjacent the catheter (not shown), and an extended position, with a distal region of the wire extended beyond the secondary lumen's distal orifice so as to bow away from the catheter shaft (shown in FIG. 8). At such extended position, a central region of the bowed portion of the wire presses against a back wall of the ventricle, as at arrows "E," thereby causing a distal region of the bowed portion to urge the catheter's distal end toward the target region of the endocardial wall, as indicated by arrow "C." In another embodiment, a region of the catheter, toward its distal end, is configured with a pre-formed (normal) bend of sufficient stiffness or rigidity to maintain the distal tip of the shaft proximate the target region of the endocardial wall, notwithstanding such "action-reaction" forces. For example, a reinforced external sleeve can be placed over the region "D" of the catheter shaft to impart the desired bend along such region. Alternatively, the bend along region "D" can be inducible from a remote position.

In general, the apparatus and method of the present invention may employ a wide variety of agents, e.g., ranging from active compounds to markers to gene therapy compounds. Exemplary agents, contemplated for use herein, are set forth in U.S. Pat. Nos. 5,840,059; 5,861,397; 5,846,946; 5,703,055; 5,693,622; 5,589,466; and 5,580,859, each incorporated entirely herein by reference. In one embodiment, for example, the invention is employed to deliver one or more genes (e.g., as so-called "naked DNA") into cavities formed into the myocardium of a subject.

In one embodiment, wherein the agent includes DNA, controlled-release preparations are formulated through the use of polymers to complex or absorb the selected gene sequence (with or without an associated carrier, e.g., liposomes, etc.). The agents can be formulated according to known methods to prepare pharmaceutically useful compositions, whereby these materials, or their functional derivatives, are combined in admixture with a pharmaceutically acceptable carrier vehicle. Suitable vehicles and their formulation, are described, for example, in Nicolau, C. et al. (Crit. Rev. Ther. Drug Carrier Syst. 6:239–271 (1989)), which is incorporated entirely herein by reference. In order to form a pharmaceutically acceptable composition suitable for effective administration, such compositions will contain an effective amount of the desired gene sequence together with a suitable amount of carrier vehicle.

Additional pharmaceutical methods may be employed to control the duration of action. Controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another method to control the duration of action by controlled release preparations is to incorporate the agent into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin microcapsules and poly(methylmethacylate) microcapsules, respectively, or in colloidal drug delivery systems, for example, liposomes, albumin microspheres, microemulsions, nanoparticles, and nanocapsules or in macroemulsions.

In a typical use, the agent will enter at one or more target regions along a surface or wall of a selected tissue, and diffuse into the tissue, aided by the action of the jets. Advantageously, the high-energy jets provided herein can be utilized even when the distal end of the apparatus (e.g., a catheter shaft) is highly deflected.

It should now be appreciated that the present invention provides a number of advantages over the prior needle-based injection systems. For example, a greater area/volume of tissue can be treated with each delivery as compared to conventional single-needle systems. Also, the present invention is greatly simplified over most of the known needle-based delivery systems. For example, the high-energy jet delivery arrangements herein do not require a reciprocally movable shaft, as required by the known needle-based delivery systems for advancing the needle into a tissue from a remote location, which can limit the useful range of action.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

It is claimed:

1. An apparatus for delivering one or more selected diagnostic or therapeutic agents to a target site within a selected body tissue, comprising:

an elongate jacket having (i) proximal and distal ends, (ii) one or more lumens extending between said ends, and (iii) a substantially blunt, distal-end face comprising (a) a plate-like member mounted substantially transverse to a longitudinal axis of said jacket at the distal end of said jacket, wherein said plate-like member defines said distal end face, and (b) one or more bores extend through said plate-like member, with each bore defining one or more outlet ports, wherein said outlet ports communicate with one or more of said lumens, and wherein each of said outlet ports have a diameter of about 0.025" or less; and a pressure-control source adapted for fluid communication with one or more of said lumens, said source being operable to establish an elevated pressure within such lumen(s) such that an agent placed therein will be propelled toward, and out of, one or more of said outlet ports, thereby forming one or more respective fluid jets or streams capable of penetrating a selected tissue disposed adjacent thereto.

2. The apparatus of claim 1, wherein each of said outlet ports has a diameter within a range of from about 0.00025" to about 0.020".

3. The apparatus of claim 1, wherein the central, longitudinal axis of at least one of said outlet ports is oriented substantially parallel to the central, longitudinal axis of said jacket at its distal end.

4. The apparatus of claim 1, wherein said jacket is adapted to withstand an internal pressure of at least about 300 psi along its proximal end, and at least about 100 psi along its distal end.

5. The apparatus of claim 1, wherein said pressure-control source is adapted to generate an internal pressure at the distal end of said jacket, proximate to said outlet ports, of at least about 20 psi.

6. The apparatus of claim 1, wherein said jacket includes a distal end region adapted for navigation through the vasculature of a subject body so that said outlet ports can be positioned adjacent a wall of such selected tissue.

7. The apparatus of claim 1, wherein at least two separate lumens extend through said jacket, each distally terminating at a fluid connection with at least one of said outlet ports.

8. The apparatus of claim 7, wherein said separate lumens are defined by respective elongate tubes extending through said jacket, with each tube having an internal passage with a diameter of from about 0.010" to about 0.020".

9. The apparatus of claim 1, further comprising an elongate catheter sleeve having (i) proximal and distal ends and (ii) one or more lumens between said ends; with one such lumen being adapted to removably receive said jacket.

10. The apparatus of claim 9, wherein said jacket-receiving lumen is further adapted to serve as a guidewire channel, when said jacket is removed therefrom.

11. The apparatus of claim 9, wherein one of said lumens, other than said jacket-receiving lumen, defines a guidewire channel.

12. The apparatus of claim 11, wherein said jacket-receiving lumen and said guidewire channel extend side-by-side from the proximal end to the distal end of said sleeve.

13. The apparatus of claim 11, wherein (i) said jacket-receiving lumen extends from the proximal end to the distal end of said sleeve, and (ii) said guidewire channel is provided near a distal end of said sleeve to enable use of said apparatus as a rapid exchange type catheter.

14. The apparatus of claim 1, further comprising means for maintaining the distal end of the jacket at such a target site while one or more high-energy fluid jets or streams are being directed thereagainst.

15. The apparatus of claim 1, further comprising one or more valves, each being disposed at location along a distal region of a respective one of said lumens for regulating fluid flow therethrough.

16. The apparatus of claim 1, further comprising an agent-holding region adapted for fluid communication with said lumen(s).

17. The apparatus of claim 1, wherein the agent is coated on a plurality of carrier micro particles.

18. The apparatus of claim 1, further comprising an ultrasonic transducer disposed across said lumen(s) along a distal-end region of said jacket.

19. The apparatus of claim 1 wherein the distal portion of the jacket is flexible and remotely steerable.

20. The apparatus of claim 1 further comprising one or more force contact tranducers located on the distal end of the jacket.

21. The apparatus of claim 1 wherein a portion of the proximal end of the jacket is substantially rigid and a portion of the distal end of the jacket is substantially flexible and either bendable or remotely steerable.

22. The apparatus of claim 1 wherein a portion of the distal end of the jacket is bent.

23. A method for delivering one or more selected diagnostic or therapeutic agents to a target site within a selected body organ or tissue, comprising:

directing one or more fluid jets or streams against a wall or surface of a selected, internal body organ or tissue, with each jet or stream (i) carrying such agent(s); (ii) having a maximum diameter of about 0.025", or less, as it contacts the wall or surface, and (iii) having an energy sufficient to permit the agent(s) to penetrate the organ or tissue to a depth of at least about 2 mm, wherein said jet fluid jet(s) or stream(s) include(s), in part, a gas that is absorbable by said selected body organ or tissue.

24. The method of claim 23, wherein said directing step is effected using an agent-delivery apparatus comprised of an elongate jacket having (a) proximal and distal ends, (b) one or more lumens extending between said ends, and (c) a substantially blunt, distal-end face defining one or more outlet ports communicating with one or more of said lumens; and wherein said agent is directed from said outlet port(s) against such wall or surface.

25. The method of claim 24, wherein each jet or stream is formed by propelling said agent(s) through at least a portion of said lumen and out of one of said outlet ports under condition of an increased pressure at said port of up to about 100 psi.

26. The method of claim 23, wherein at least one jet or stream is directed substantially along a line angled no greater than about 35 degrees in respect to a line normal to such wall or surface.

27. The method of claim 23, wherein at least one jet or stream is directed substantially along a line normal to such wall or surface.

28. The method of claim 23, wherein the selected tissue is myocardial tissue, and the selected agent is directed against an endocardial wall, a septal wall, or an epicardial wall from a distance no greater than about 5 mm from such wall.

29. The method of claim 28, wherein the selected agent has angiogenic properties.

30. The method of claim 28, wherein the selected agent includes a nucleic acid or a protein.

31. The method of claim 30, wherein the selected agent includes a nucleic acid carried on micro-particles.

* * * * *

UNITED STATES PATENT AND TRADEMARK OFFICE
CERTIFICATE OF CORRECTION

PATENT NO. : 6,641,553 B1
DATED : November 4, 2003
INVENTOR(S) : Chee et al.

It is certified that error appears in the above-identified patent and that said Letters Patent is hereby corrected as shown below:

Title page,
Item [73], Assignee: "Boston Scientific Corporation, Natick, MA" should be
-- Scimed Life Systems, Inc., Maple Grove, MN --.

Signed and Sealed this

Thirteenth Day of April, 2004

JON W. DUDAS
*Acting Director of the United States Patent and Trademark Office*